United States Patent [19]

Levine

[11] 4,203,551
[45] May 20, 1980

[54] APPARATUS FOR PRODUCING A PULSATING SPRAY OF WATER

[76] Inventor: Stewart A. Levine, 30-1 Farm Rd., Somerville, N.J. 08876

[21] Appl. No.: 938,633

[22] Filed: Aug. 31, 1978

[51] Int. Cl.² ............................................. B65N 75/00
[52] U.S. Cl. ...................................... 239/195; 239/444
[58] Field of Search .............. 239/195, 101, 102, 443, 239/444, 588, 381, 130, 574, 530

[56] References Cited

U.S. PATENT DOCUMENTS

| 2,588,255 | 3/1952 | Larsh ..................................... 239/44 |
| 4,151,957 | 5/1979 | Gecewicz ............................ 239/530 |

Primary Examiner—James B. Marbert
Attorney, Agent, or Firm—Carella, Bain, Gilfillan & Rhodes

[57] ABSTRACT

An apparatus for non-electrically producing a pulsating spray of water which may be directed to various body cavities as well as any other selected portions of the body. The apparatus is utilized in conjunction with a water supply system and is connected thereto in such a way as to not interfere with the normal flow of water through said water supply system. A flexible tube is utilized for communicating water from said water supply system to a tip for facilitating the aiming of a pulsating spray of water at any desired portion of a body.

4 Claims, 4 Drawing Figures

APPARATUS FOR PRODUCING A PULSATING SPRAY OF WATER

BACKGROUND OF THE INVENTION

1. Field of the Invention

The invention relates generally to apparatus for communicating water from one point to another. More specifically, the invention relates to apparatus for producing a pulsating flow of water out of the end of a flexible tube.

2. Description of the prior art

Apparatus for producing a pulsating spray or flow of water is known in the prior art. Furthermore, prior art apparatus exist wherein the pulsating of the water is achieved by a non-electrically operative means. Prior art apparatus is also known wherein the pulsating spray of water is presented at the end of a flexible tube.

Generally, the prior art apparatus for producing a pulsating spray of water are connected to the terminal end of the faucet outlet of a water supply sustem. Such connection of the prior art apparatus to the terminal end or faucet outlet of the water supply system prevents the normal flow of water out of the system from occurring simultaneously with the pulsating flow of water emerging from said apparatus for producing a pulsating spray of water. Thus, prior art apparatus for producing a spray of water must be disconnected after each use in order to enable normal use of the water supply system. This is inconvenient and often cumbersome.

Furthermore, prior art apparatus for producing a pulsating spray of water are generally utilized for the removal of interproximal debris and plaque from teeth and the cleaning of the oral cavity in general, and are utilized by a user by attachment to the water faucet of a sink. While such prior art apparatus does consist of a flexible tube which enables the direction of water spray into the oral cavity, the continual spray of water from said flexible tube creates a generally undesirable and unaesthetic situation because of the unavoidable dribbling of spent water from the oral cavity over the user's clothing and over the sink, floor, etc. Additionally, such prior art apparatus is similarly undesirable and unacceptable for the hygienic maintenance of other body cavities and surfaces. For example, prior art apparatus is unacceptable for douching, cleaning the anal and perianal areas and for rinsing and irrigating the ear.

Accordingly, there exists a need for an apparatus for producing a pulsating spray of water while simultaneously enabling the normal flow of water from the water supply system to which the water spray apparatus is connected. Such simultaneity would facilitate the use of said apparatus by obviating the necessity of disconnecting an apparatus for producing a pulsating spray of water from a water supply system in order for the system to be used in the normal fashion.

Additionally, there exists a need for an apparatus for producing a pulsating spray of water which may be utilized in a shower, bathtub, or the like, thereby eliminating the undesirable and unaesthetic qualities associated with use of such apparatus in a sink. Furthermore, use of such apparatus in a shower or tub will expand the range of acceptable uses of such apparatus by enabling the cleansing of any desired body cavities or surfaces with no attendant objectionable effects such as dribbling, etc.

SUMMARY OF THE INVENTION

The present invention provides water spray apparatus including a flexible tube one end of which is connected to a tip and the other end of which is connected to a water supply, such as for example a shower head or pipe associated therewith or to a faucet in a tub, such that the flexible hose is communicated with the normal flow of water through the water supply system and whereby water may emerge simultaneously from the shower head, pipe or faucet in the normal fashion and also from the tip; in one embodiment the flexible hose is connected substantially perpendicular to the passageway through the water supply system.

The invention eliminates the problems presented by prior art apparatus because it enables use of a shower head, or the like while simultaneously enabling use of the apparatus for producing a pulsating spray of water.

Accordingly, an object of the invention is to provide an apparatus for producing a pulsating spray of water which may be utilized whenever desired and without the necessity for connection to a water supply system for each desired use and for disconnection subsequent to each use for enabling normal use of the water supply system.

DESCRIPTION OF THE PREFERRED EMBODIMENT

Figure 1:
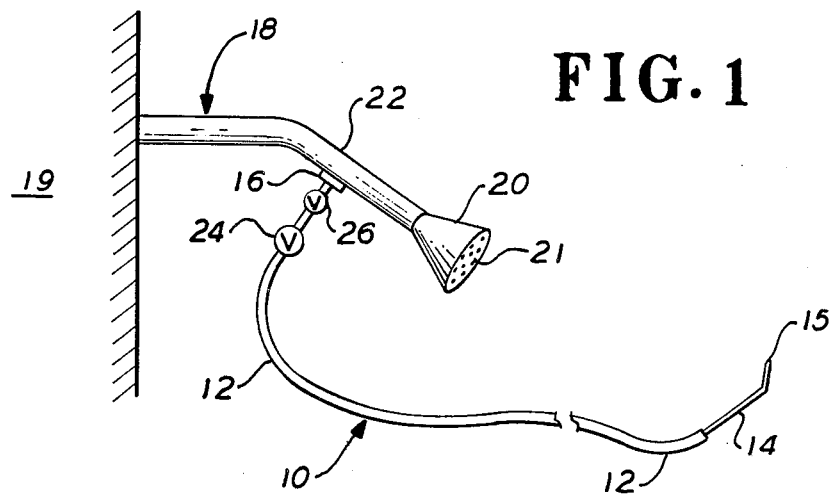
FIG. 1 is a diagrammatic side elevation view of one embodiment of the invention interconnected with a water pipe.

Referring now to the drawings, there is shown an apparatus for producing a pulsating spray of water generally designated by the numeral 10.

Referring more specifically to FIG. 1, the apparatus 10 comprises a flexible tube 12 having a tip 14 at one end thereof. As will be understood by those skilled in the art, tip 14 may be detachably secured to tube 12 so that varying types of tips may be utilized in apparatus 10, depending upon the surface or cavity intended to be cleaned. Tip 14 has an aperture 15 through which water will flow. The other end of flexible tube 12 is connected, via connecting means 16, to a water supply system 18 mounted adjacent a wall 19 of a shower stall (not shown) or a bathtub (not shown). While the water supply system shown in FIG. 1 is shown associated with a shower head 20 supplied by a water pipe 22, it will be understood by those skilled in the art that any suitable water supply system may be utilized. Thus, shower head 20 may be considered equivalent to a faucet or the like. Furthermore, it is noted that in order to facilitate construction, connecting means 16 is interconnected with said water pipe 22 such that tube 12 is generally perpendicular to the longitudinal axis (not shown) of water pipe 22. However, it will be understood by those skilled in the art that interconnection may occur at any predetermined point on said water supply system 18 and even on shower head 20 (as will be seen in FIG. 2).

In the embodiment shown in FIG. 1, shower head 20 is a normal shower head for producing a normal spray of water (i.e. non-pulsating) by means of apertures 21. Accordingly, a pulsating valve means 24 must be included intermediate (or on) connecting means 16 and (or) aperture 15 in order to produce a pulsating spray of water out of said tip 14. It will be under stood by those skilled in the art that valve means 24 may be situated at any point intermediate connecting means 16 and aperture 15.

It will be further understood by those skilled in the art that pulsating valve means 24 should be a non-electrically operative pulsating means in view of safety hazards presented by the use of electrical devices in a water environment. Accordingly, any suitable non-electrical pulsating means may be utilized such as periodically activated pressure-sensitive valves or other fluidic devices, etc.

Upon the flow of water through said water supply system 18 and therefore out of shower head 20 (or, for example, a faucet associated with a bathtub), pulsating water will spray simultaneously from aperture 15. A valve 26 may be interposed anywhere between connecting means 16 and aperture 15 in order to interrupt said pulsating flow of water when desired.

While the above description has centered about the use of a normal, non-pulsating shower head 20, it will be apparent to those skilled in the art that apparatus 10 could equally well be utilized in conjunction with a shower head (not shown) that is capable of producing a pulsating spray of water out of aperture 21. In that event, connecting means 16 may be connected to such a pulsating shower head at a point where pulsating water may be communicated through tube 12 to tip 14 without the need for a pulsating valve 24. However, a pulsating valve 24 could be utilized in conjunction with such a pulsating shower head whereby the configuration of apparatus 10 would be that shown in FIG. 1. Thus, it will be apparent to those skilled in the art that the apparatus 10 shown in FIG. 1 may be utilized as previously described, regardless whether shower head 20 is a pulsating or non-pulsating type of shower head, and regardless whether shower head 20 is a faucet having only one aperture as opposed to a shower head having a plurality of apertures.

Figure 1A:
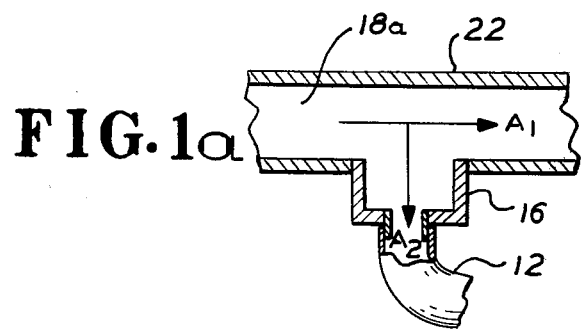
FIG. 1A is an enlarged cross-sectional view of a portion of FIG. 1.

FIG. 1a is an enlarged cross-sectional view of a portion of FIG. 1. More specifically, FIG. 1a is a view of the longitudinally extending passageway 19 within water pipe 22 and the interconnection therewith of connecting means 16 and flexible tube 12. The direction of the normal flow of water in passageway 19 is diagrammatically illustrated in arrow $A_1$. The apparatus disclosed herein permits water to flow in direction $A_2$ simultaneously with the flow in direction $A_1$.

Figure 2:
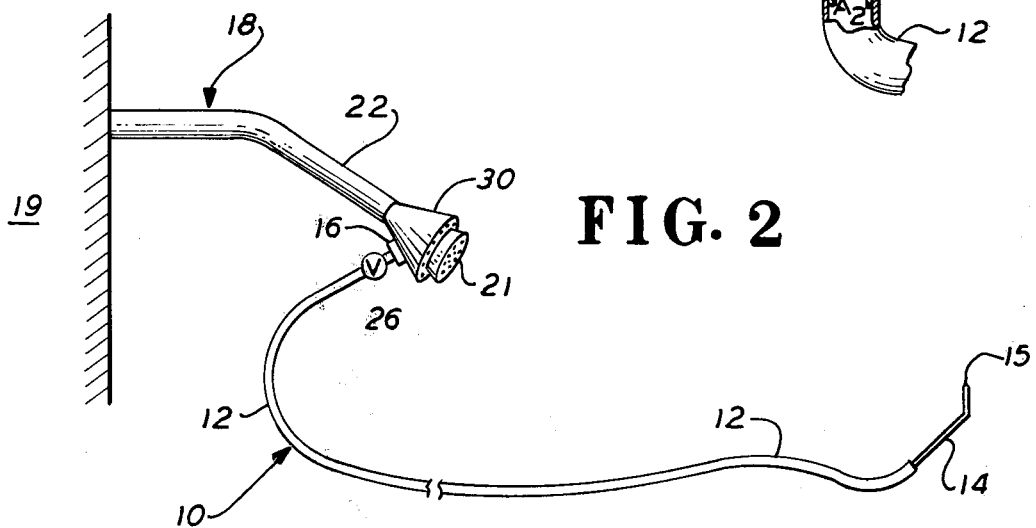
FIG. 2 is a diagrammatic side elevation view of an alternate embodiment of the invention interconnected with a shower head.

Referring now to FIG. 2, apparatus 10 is shown interconnected with a pulsating (e.g. massaging) type of shower head 30. Accordingly, there is no need for a pulsating valve means 24 in the embodiment shown in FIG. 2 because pulsating water is normally produced by shower head 30. Thus, substantially all elements of the embodiment shown in FIG. 2 are shown and numbered identically with those of FIG. 1 since the distinction between the two embodiments is essentially the point of interconnection of the apparatus 10 with the water supply system. FIG. 2 is disclosed herein for the purpose of manifesting the use of the invention in conjunction with a massaging or pulsating shower head.

Figure 2A:
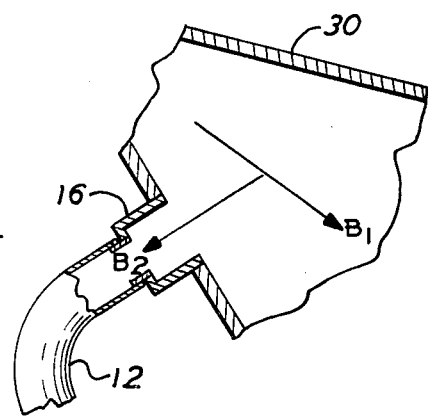
FIG. 2A is an enlarged cross-sectional view of a portion of FIG. 2.

FIG. 2a is an enlarged cross-sectional view of a portion of FIG. 2 and is analogous to FIG. 1a: normal flow of water in shower head 30 is represented by arrow $B_1$, and the simultaneous flow enabled by the apparatus disclosed herein is represented by $B_2$.

It will be noted and understood that the apparatus for producing a spray of water, as disclosed herein, will enable the normal flow of water from a water supply source while simultaneously enabling a pulsating spray of water from the apparatus.

It will be understood by those skilled in the art that many other modifications, embodiments and variations may be made of the invention disclosed herein without departing from the spirit and scope thereof.

What is claimed is:

1. Apparatus for producing a pulsating spray of water for lavaging of body orifices, said apparatus for being connected to a water supply system for providing a normal flow of water therethrough, comprising:

a tip;

a flexible tube one end of said tube connected to said tip and said tube for communicating water from said water supply system to said tip;

connecting means connected to the other end of said flexible tube and for interconnecting said flexible tube to said water supply system so as to simultaneously allow said normal flow of water through said supply system and a flow of water through said flexible tube and out of said tip; and pulsating means positioned intermediate said connecting means and said tip and for pulsating said water communicated through said flexible tube and out of said tip.

2. Apparatus for producing a spray of water for lavaging of body orifices, said apparatus for being connected to a water faucet without interrupting the normal flow of water through said faucet, said water faucet having a generally lontitudinally extending passageway therethrough for communicating water through and out of said faucet, comprising:

a tip;

a flexible tube for communicating water from said water faucet to said tip;

connecting means for interconnecting with said faucet at a predetermined point substantially perpendicular to said passageway through said water faucet and for communicating said longitudinally extending passageway within said flexible tube;

one end of said flexible tube connected to said tip and the other end of said flexible tube connected to said connecting means; and upon the flow of water through said passageway provided in said water faucet, a portion of said water being communicated into said interconnecting means for communication through said flexible tube to and out of said tip.

3. Apparatus according to claim 2 wherein said apparatus for producing a spray of water further includes pulsating means positioned intermediate said interconnecting means and said tip and for pulsating said water communicated through said flexible tube and out of said tip.

4. Apparatus according to claim 3 wherein said pulsating means is a non-electrically operated pulsating means.

* * * * *